(12) United States Patent
Liang et al.

(10) Patent No.: US 8,053,222 B2
(45) Date of Patent: Nov. 8, 2011

(54) PROTEIN EXPRESSION SYSTEM INVOLVING MUTATED SEVERE RESPIRATORY SYNDROME-ASSOCIATED CORONAVIRUS 3C-LIKE PROTEASE

(75) Inventors: Po-Huang Liang, Taipei (TW);
Chih-Jung Kuo, Taipei County (TW);
Yan-Ping Shih, Kaohsiung County (TW)

(73) Assignee: Academia Sinica, Taiwan, Taipei (TW)

( * ) Notice: Subject to any disclaimer, the term of this patent is extended or adjusted under 35 U.S.C. 154(b) by 70 days.

(21) Appl. No.: 12/370,118

(22) Filed: Feb. 12, 2009

(65) Prior Publication Data

US 2010/0203582 A1 Aug. 12, 2010

(51) Int. Cl.
*C12N 9/48* (2006.01)
*C12N 15/00* (2006.01)
*C12P 21/06* (2006.01)
*C07H 21/04* (2006.01)

(52) U.S. Cl. ... 435/212; 435/68.1; 435/69.1; 435/320.1; 536/23.2; 536/23.1

(58) Field of Classification Search ............... 435/212, 435/68.1, 69.1, 320.1; 536/23.2, 23.1
See application file for complete search history.

(56) References Cited

U.S. PATENT DOCUMENTS

| 5,087,564 A | 2/1992 | Mai et al. |
| 5,427,927 A | 6/1995 | Meyer et al. |
| 6,010,883 A | 1/2000 | Nagai et al. |
| 2006/0199251 A1 | 9/2006 | Lorentsen et al. |

OTHER PUBLICATIONS

Chen et al., Only one promoter is active in the dimer of SARS 3C-like proteinase. J. Biol. Chem., 2006, vol. 281(20): 13894-13898.*
Devos et al., Practical limits of function prediction. Proteins: Structure, Function, and Genetics. 2000, vol. 41: 98-107.*
Shi et al., The catalysis of the SARS 3C-like protease is under extensive regulation by its extra domain. FEBS Journal. 2006, vol. 273: 1035-1045.*
Wei et al. The N-terminal octapeptide acts as a dimerization inhibitor of SARS coronavirus 3C-like protease. Biochim Biophys Res Commun., 2006, vol. 339: 865-872.*
Whisstock et al., Prediction of protein function from protein sequence. Q. Rev. Biophysics., 2003, vol. 36 (3): 307-340.*
Chica et al., Semi-rational approaches to engineering enzyme activity: combining the benefits of directed evolution and rational design. Curr. Opi. Biotechnol., 2005, vol. 16: 378-384.*
Guo et al., Protein tolerance to random amino acid change. PNAS., 2004, vol. 101 (25): 9205-9210.*
Kimchi-Sarfaty et al., A "Silent" polymorphism in the MDR1 gene changes substrate specificty. Science, 2007, vol. 315: 525-528.*
Nackley et al., Human Caechol-O-Methytransferase haplotypes modulate protein expression by altering mRNA secondary structure. Science, 2006, vol. 314: 1930-1933.*
Sauna et al., Silent polymorhisms speak: How they affect pharmacogenomics and the treatment of cancer. Cancer Res., 2007, vol. 67(20): 9609-9612.*
Sen et al., Developments in directed evolution for improving enzyme functions. Appl. Biochem. Biotechnol., 2007, vol. 143: 212-223.*

* cited by examiner

*Primary Examiner* — Ganapathirama Raghu
(74) *Attorney, Agent, or Firm* — Wolf, Greenfield & Sacks, P.C.

(57) ABSTRACT

A mutated severe acute respiratory syndrome-associated coronavirus 3C-like protease and use thereof for cleaving a protein that includes a cleavage site recognizable by the mutated protease to yield a polypeptide fragment of interest.

12 Claims, 2 Drawing Sheets

PROTEIN EXPRESSION SYSTEM INVOLVING MUTATED SEVERE RESPIRATORY SYNDROME-ASSOCIATED CORONAVIRUS 3C-LIKE PROTEASE

BACKGROUND OF THE INVENTION

Fusion protein technology, i.e., expressing in a host cell a target protein fused with a protein tag, confers several advantages. For example, many protein tags increase water-solubility and facilitate purification of their fusion partners. Further, several protein tags serve as protein chaperons to guide proper folding of the target proteins fused to them, thereby increasing the yields of the target proteins in native form.

One the other hand, fusion protein technology is disadvantaged in that protein tags often interfere with the structural or functional properties of the target proteins. Thus, they need to be removed via, e.g., chemical or enzymatical cleavage, from fusion proteins to release the target proteins. Cleavage of a fusion protein to remove the protein tag remains a major challenge in fusion technology as imprecise cleavage would result in failure to recover a structurally intact target protein.

SUMMARY OF THE INVENTION

The present invention is based on the unexpected discovery that replacing T at position 25 ($T_{25}$) in the severe acute respiratory syndrome-associated coronavirus 3C-like protease (SARS-CoV $3CL^{pro}$) with G alters the substrate specificity of the protease.

Accordingly, one aspect of this invention relates to a SARS-CoV $3CL^{pro}$ mutant, in which the $T_{25}$ residue in the wild-type SARS-CoV $3CL^{pro}$ is replaced by G. This mutant recognizes the cleavage site $P_4P_3P_2QP_{1'}$, (SEQ ID NO:36), in which each of $P_4$ and $P_3$, independently, is A, V, G, L, or I, $P_2$ is L, V, or F, and P1' is G, A, V, L, I, S, T, M, C, D, E, Q, N, W, Y, or F, and cleaves between Q and P1'. In one example, the cleavage site is ALVQM (SEQ ID NO:3). The SARS-CoV $3CL^{pro}$ mutant can have an amino acid sequence at least 90% (e.g., 95%) identical to that of its wild-type counterpart (SEQ ID NO:1). In one example, the mutant has the amino acid sequence of SEQ ID NO:2. Also disclosed herein is a nucleic acid that encodes the SARS-CoV $3CL^{pro}$ mutant.

Another aspect of this invention relates to use of the above-described SARS-CoV $3CL^{pro}$ mutant to cleave a polypeptide that contains the cleavage site $P_4P_3P_2QP_{1'}$ (SEQ ID NO:36) also described above. Preferably, the polypeptide is a fusion protein containing a protein tag and a target protein. The cleavage site $P_4P_3P_2QP_{1'}$ (SEQ ID NO:36) is located at the junction of the protein tag and the target protein, P1' being the N-terminal amino acid residue of the target protein. When contacted with the SARS-CoV $3CL^{pro}$ mutant, the fusion protein is cleaved by this protease to release the target protein.

In yet another aspect, the present invention features an expression vector for producing the polypeptide mentioned above. This expression vector includes a first nucleotide sequence that encodes the amino acid sequence of $P_4P_3P_2Q$ (SEQ ID NO:37), in which each of $P_4$ and $P_3$, independently, is A, V, G, L, or I and $P_2$ is L, V, or F. The 3' end of the first nucleotide sequence is a restriction site (e.g., Pst I) for cloning a nucleotide sequence encoding a target protein. In one example, the amino acid sequence $P_4P_3P_2Q$ is AVLQ (SEQ ID NO:4), which can be encoded by the nucleotide sequence of GCGGTGCTGCAG (SEQ ID NO:5). The expression vector can further include a second nucleotide sequence encoding a protein tag and optionally, a third nucleotide sequence encoding a target protein. The second nucleotide sequence is located upstream to the first nucleotide sequence while the third nucleotide sequence is located downstream to it. The first and the third nucleotide sequences, taken together, encode a polypeptide including the cleavage site $P_4P_3P_2QP_{1'}$, (SEQ ID NO:36) described above, $P_{1'}$, being the N-terminus amino acid residue of the target protein encoded by the third nucleotide sequence.

Also within the scope of this invention is a kit for producing a recombinant target protein, including the expression vector described above and the SARS-CoV $3CL^{pro}$ mutant also described above.

The details of one or more embodiments of the invention are set forth in the description below. Other features or advantages of the present invention will be apparent from the following drawings and detailed description of several embodiments, and also from the appended claims.

DETAILED DESCRIPTION OF THE INVENTION

Figure 1:
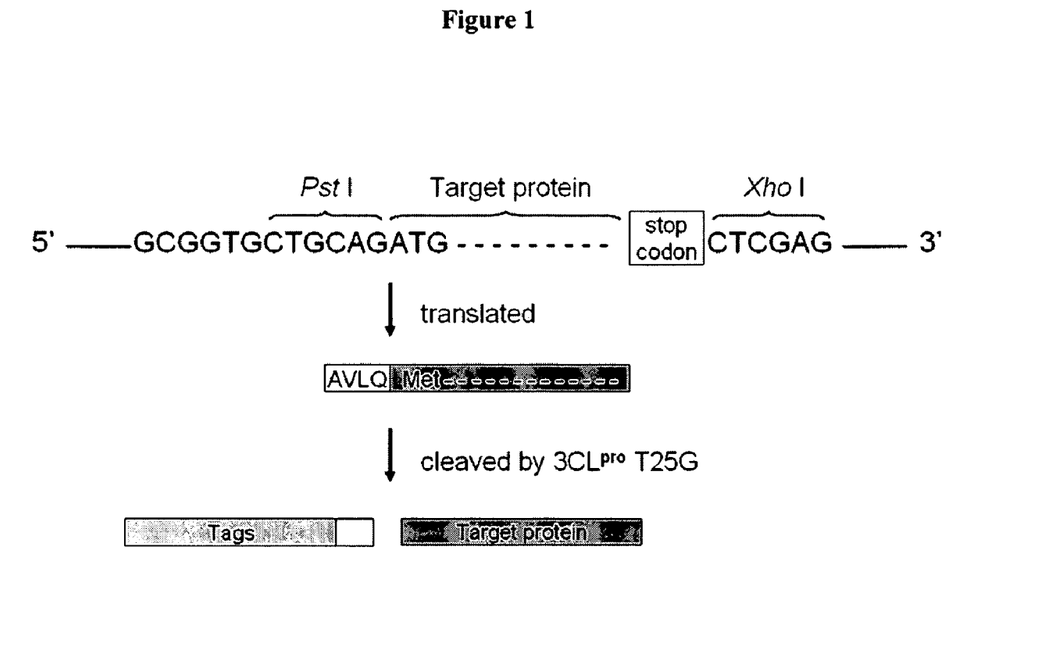
FIG. 1 is a schematic diagram showing a protein expression system. In this system, a fusion protein, including one or more protein tags, a protease cleavage site AVLQM (SEQ ID NO:6), and a target protein, is expressed and then treated with a SARS-CoV $3CL^{pro}$ mutant, i.e., T25G, to release the target protein. 'GCGGTGCTGCAGATG' is disclosed as SEC) ID NO: 35.

Described herein is a protein expression system, in which a target protein is initially expressed as a fragment of a fusion protein and then released from the fusion protein via cleavage by a mutated SARS-CoV $3CL^{pro}$. See FIG. 1.

In this system, a fusion protein containing a target protein can be produced in suitable host cells (e.g., E. coli cells, yeast cells, insect cells, and mammalian cells) by conventional recombinant technology. More specifically, a nucleotide sequence encoding the target protein can be isolated from its natural source via, e.g., polymerase chain reaction, and then cloned into an expression vector for protein production. The term "expression vector" used herein refers to a DNA plasmid that includes a promoter sequence operably linked to an encoding nucleotide sequence. A promoter sequence is a nucleotide sequence containing elements that initiates the transcription of an operably linked nucleic acid sequence. At a minimum, a promoter contains an RNA polymerase binding site. It can further contain one or more enhancer elements which, by definition, enhances transcription, or one or more regulatory elements that control the on/off status of the promoter.

The expression vector used in the protein expression system described herein is designed for expressing a fusion protein, in which a target protein is linked to one or more suitable protein tags (e.g., hexa-His; SEQ ID NO:7), the starch-binding domain of fungi glycomylase, maltose binding protein, N-utilizing substance A, thioredoxin, calmodulin-binding protein, glutathione 5-transferase, and α-factor). The junction region of a protein tag and the target protein has the amino acid sequence of $P_4P_3P_2Q\downarrow P_{1'}$ (SEQ ID NO:36) described above, $P_{1'}$ being the N-terminal residue of the target protein. Preferably, the nucleotide sequence encoding residues $P_2Q$ is also a restriction site for cloning a nucleotide sequence encoding the target protein. In one example, the junction region has the amino acid sequence of AVLQM (SEQ ID NO:6), in which LQ is encoded by the nucleotide sequence of CTGCAG, a Pst I site. See FIG. 1. The fusion protein described above is then treated with the mutated SARS-CoV $3CL^{pro}$ described herein, which recognizes the cleavage site $P_4P_3P_2QP_{1'}$ (SEQ ID NO:36) and cut between Q and $P_{1'}$, to release the target protein.

The mutated SARS-CoV $3CL^{pro}$ is derived from the wild-type SARS-CoV $3CL^{pro}$ having the amino acid sequence of SEQ ID NO:1 shown below:

```
Amino acid sequence of wild-type SARS-CoV 3CLpro
                                                     (SEQ ID NO: 1)
sgfrkmafps gkvegcmvqv tcgtTtlngl wlddtvycpr hvictaedml        50 npnyedllir ksnhsflvqa gnvqlrvigh smqncllrlk vdtsnpktpk       100 ykfvriqpgq tfsvlacyng spsgvyqcam rpnhtikgsf lngscgsvgf       150 nidydcvsfc ymhhmelptg vhagtdlegk fygpfvdrqt aqaagtdtti       200 tlnvlawlya avingdrwfl nrftttlndf nlvamkynye pltqdhvdil       250 gplsaqtgia vldmcaalke llqngmngrt ilgstilede ftpfdvvrqc       300 sgvtfq
```

The wild-type SARS-CoV $3CL^{pro}$ is a protease that specifically recognizes the cleavage site of AVLQS (SEQ ID NO:8) and cleaves between Q and S. We have discovered that the T residue at position 25 ($T_{25}$; capitalized and boldfaced) in SEQ ID NO:1 is critical in determining substrate specificity of the protease. The SARS-CoV $3CL^{pro}$ mutant disclosed herein has a G residue, instead of T, at the position corresponding to position 25 in SEQ ID NO:1. This mutant has an amino acid sequence at least 80% (e.g., 85%) identical to SEQ ID NO:1 and recognizes the cleavage site $P_4P_3P_2QP_{1'}$ (SEQ ID NO:36) described above. In one example, the SARS-CoV $3CL^{pro}$ mutant has the following amino acid sequence:

```
Amino acid sequence of SARS-CoV 3CLpro mutant
                                                     (SEQ ID NO: 2)
sgfrkmafps gkvegcmvqv tcgtGtlngl wlddtvycpr hvictaedml        50 npnyedllir ksnhsflvqa gnvqlrvigh smqncllrlk vdtsnpktpk       100 ykfvriqpgq tfsvlacyng spsgvyqcam rpnhtikgsf lngscgsvgf       150 nidydcvsfc ymhhmelptg vhagtdlegk fygpfvdrqt aqaagtdtti       200 tlnvlawlya avingdrwfl nrftttlndf nlvamkynye pltqdhvdil       250 gplsaqtgia vldmcaalke llqngmngrt ilgstilede ftpfdvvrqc       300 sgvtfq
```

While the wild-type SARS-CoV $3CL^{pro}$ does not recognize a cleavage site of $P_4P_3P_2QP_{1'}$ (SEQ ID NO:36), where $P_{1'}$ is an amino acid residue with a bulky side chain (e.g., M and L), the mutated protease recognizes such a cleavage site and cut precisely between Q and $P_{1'}$.

The SARS-CoV $3CL^{pro}$ mutant can be prepared by conventional methods, e.g., mutagenesis technology. For example, mutations can be introduced into a nucleotide sequence encoding the wild-type SARS-CoV $3CL^{pro}$ so that the codon encoding $T_{25}$ in the wild-type protease is replaced with a codon encoding G. The nucleotide sequence carrying the mutations can then be inserted into an expression vector and its encoding SARS-CoV $3CL^{pro}$ mutant can be expressed in a suitable host cell. Upon purification, the mutant can be analyzed to confirm the protease activity and substrate specificity by conventional methods, some of which are described in Examples 1 and 2 below.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. All publications cited herein are incorporated by reference.

Example 1

Preparation of $3CL^{pro}$ Mutant T25G

A DNA fragment encoding the wild-type SARS-CoV $3CL^{pro}$ was cloned into pET32Xa/Lic vector and expressed in *E. coli*; the protease thus obtained was purified from the host cell following the methods described in Kuo et al., *Biochem. Biophys. Res. Comm.* 318:862-867 (2004).

The nucleotide sequence encoding the wild-type SARS $3CL^{pro}$ was subjected to mutagenesis to produce a nucleotide sequence encoding the mutated SARS-CoV $3CL^{pro}$ T25G using the QuickChange site-directed mutagenesis kit (Invitrogen). More specifically, a DNA fragment encoding the T25G mutant was obtained by polymerase chain amplification (PCR) using the nucleotide sequence encoding the wild-type SARS-CoV $3CL^{pro}$ as a template and the primers shown below:

Forward primer: 5'-GGTGCATGGTACAAGTAACCT-GTGGAACTGGAACTCTTAA TGGAT TGTGGTTGG-3' (SEQ ID NO: 9); (the underlined nucleotides referring to the mutated codon).

Reverse primer: 5'-CCAACCACAATCCATTAAGAGT-TCCAGTTCCACAGGTTACT TGTACCATGCACC-3' (SEQ ID NO: 10) (the underlined nucleotides referring to the mutated codon).

After being treated with DpnI to remove those that contain the wild-type SARS-CoV 3CL$^{pro}$ gene, the PCR products were introduced into E. coli BL21 host cells and positive transformants were selected. Plasmids, isolated from those transformants, were analyzed by DNA sequencing to confirm that they included the nucleotide sequence encoding the T25G mutant. After confirmation, the transformants were cultured under suitable conditions for expression of the T25G mutant.

The DNA fragment encoding the T25G mutant was used as a template for producing a DNA fragment encoding His-tagged T25G, using the primers:

```
Forward primer:
5'-CATGCCATGGCCAGTGGTTTTAGGAAAATGGCATTCCCG-3'
(SEQ ID NO: 11); and Reverse primer:
5'-CCGCTCGAGCGGTCAATGATGATGATGATGATGTTGGAAGGTAACAC
CAGAGCA-3'(SEQ ID NO: 12).
```

The underlined regions refer to the restriction sites of Nco I and Xho I. The PCR product was cloned into the pET16b vector (Novagen) via the Nco I and Xho I cloning sites. The resultant pET16b-His-T25G plasmid was introduced into E. coli BL21(DE3) for expression of His-tagged T25G.

The wild-type SARS-CoV 3CL$^{pro}$, T25G mutant, and His-tagged T25G, expressed in E. coli host cells, were purified and then analyzed for their protease activity and substrate specificity as follows.

The protease activity of the three proteins were determined using a fluorogenic substrate Dabcyl-KTSAVLQSGFRKME-Edans (SEQ ID NO: 13). See Kuo et al., 2004. This substrate includes the native cleavage site of SARS-CoV 3CL$^{pro}$ (highlighted), which cleaves between Q (position P$_1$) and S (position P$_1$'). Both T25G and His-T25G exhibited similar protease activity in cleaving the just-noted substrate as compared to the wild-type SARS-CoV 3CL$^{pro}$. This result indicated that the T→G mutation at position 25 in the wild-type SARS-CoV 3CL$^{pro}$ does not affect the protease activity.

To determine substrate specificity of the wild-type SARS-CoV 3CL$^{pro}$ and the T25G mutant, either protein was mixed with each of the ten substrates listed below:

|     | P$_4$P$_3$P$_2$P$_1$P$_1$' |               |
|-----|-----------------------------|---------------|
| (1) | SAVLQSGFRK,                 | (SEQ ID NO: 14) |
| (2) | SAVLQAGFRK,                 | (SEQ ID NO: 15) |
| (3) | SAVLQGGFRK,                 | (SEQ ID NO: 16) |
| (4) | SAVLQHGFRK,                 | (SEQ ID NO: 17) |
| (5) | SAVLQKGFRK,                 | (SEQ ID NO: 18) |
| (6) | SAVLQLGFRK,                 | (SEQ ID NO: 19) |
| (7) | SAVLQMGFRK,                 | (SEQ ID NO: 20) |
| (8) | SAVLQPGFRK,                 | (SEQ ID NO: 21) |
| (9) | SAVLQEGFRK,                 | (SEQ ID NO: 22) and |
| (10) | SAVLQFGFRK                 | (SEQ ID NO: 23). |

These peptide substrates were synthesized using a 433A peptide synthesizer (Applied Biosystems, USA) as follows. Starting with 0.10 mmol (0.101 g) of p-hydroxymethyl phenoxymethyl polystyrene resin (1.01 mmol/g), the synthesis of the peptides was performed using a stepwise FastMoc protocol (Applied Biosystems, USA). The amino acids were introduced using the manufacturer's prepacked cartridges (1 mmol each).

To analyze the substrate specificity of the wild-type SARS-CoV 3CL$^{pro}$ and the T25G mutant, each of the peptide substrates (100 µM) was incubated with 0.1 µM protease for 1, 2, and 6 h, and the reaction products were analyzed by HPLC using a C-18 reverse-phase analytic column (Vydac) to determine whether the substrate was cleaved.

The results obtained from this study indicate that both the wild-type SARS-CoV 3CL$^{pro}$ and the T25G mutant recognized the cleavage sites where position P$_1$' is a small amino acid residue, i.e., G and S, and both proteases did not recognize the cleave sites where position P$_1$' is H, K, or P. The results also indicated that T25G cleaved substrates 1, 2, 6, and 7, which contain the cleave sites where position P$_1$' is E, F, L, and M, while the wild-type SARS-CoV 3CL$^{pro}$ did not cleave these substrates.

Next, the kinetics of the protease activity of both the wild-type SARS-CoV 3CL$^{pro}$ and the T25G mutant were determined as follows, using peptide SAVLQMGFRK (SEQ ID NO: 20) as the substrate, i.e., Substrate (7). The cleavage products were resolved using a 30 min, 2-90% liner gradient of acetonitrile supplemented with 0.1% TFA. The areas of the product peaks, determined by HPLC analysis, were integrated to calculate the reaction rate of either wild-type SARS-CoV 3CL$^{pro}$ (0.1 µM) or the T25G mutant (0.1 µM) for cleaving each substrate at various concentrations (10-200 µM). A reaction curve for each protein was drawn based on the reaction rates versus substrate concentrations and the kinetic parameters (i.e., $k_{cat}$ and $K_m$) were determined based on the reaction curve using Michaelis-Menten equation fitted with the KaleidaGraph computer program. The results are shown below:

Wild-type SARS-CoV 3CL$^{pro}$: $k_{cat}$ is 1.6±0.2 min$^{-1}$ and $K_m$ is 76.6±3.5 µM ($k_{cat}/K_m$=0.02 µM$^{-1}$ min$^{-1}$).

T25G mutant: $k_{cat}$ is 16.2±0.5 min$^{-1}$ and $K_m$ is 18.6+2.4 µM ($k_{cat}/K_m$=0.87 04 µM$^{-1}$ min$^{-1}$).

The catalytic efficiency of the T25G mutant in cleaving SAVLQMGFRK (SEQ ID NO: 20) was 43.5-fold higher than that of the wild type.

Example 2

Preparation of Target Proteins with Protein Expression System Involving SARS-CoV 3CL$^{pro}$ Mutant T25G A yeast expression vector, pHTPY6, for expression a fusion protein, was constructed as follows. Two oligonucleotides: 5'-TCGAAAAAAGAGAGGCTGAAGCTGAATTCTGCA GCTCGAGCGTGGCCCAGCCGGC-CGTCTCGGATCGGTACG-3' (SEQ ID NO: 24) and 5'-TCGACGTACCGATCCGAGACGGCCGGCTGGGCCA-CGCTCGAGCTGCAGA ATTCAGCTTCAGC-CTCTCTTTTT-3' (SEQ ID NO: 25) were annealed to form a double-stranded fragment including an EcoR I and an Xho I sites, as well as two mutated Xho I sites (underlined). The fragment was then phosphorylated and inserted into pPIC-ZαA (Invitrogen) via the two Xho I cloning sites contained therein to form the pHTPY1 vector. In this vector, the two Xho I sites (CTCGAG) contained in pPICZ☐A were replaced by the nucleotide sequences CTCGAA and CTCGAC, both of which could no longer be digested by Xho I.

Next, the pHTPY6 vector was further modified to insert a nucleotide sequence that encodes a His-tag and the SARS- CoV 3CL$^{pro}$ recognition sequence Ala-Val-Leu-Gln (SEQ ID NO: 4). Two oligonucleotides: 5'-AATTCACGGGTAC-CGCCCAGCCGGCCCACCACCACCACCACC ACG-GAGGAGGAACTAGTGCGGTGCTGCAGC-3' (SEQ ID NO: 26) and 5'-TCGAGCTGCAGCACCGCA CTAGTTC-CTCCTCCGTGGTGGTGGTGGTG GTGGGCCG-GCTGGGCGGTACCCGTG-3' (SEQ ID NO: 27) were annealed to form a double-stranded fragment, the fragment being phosphorylated and then inserted into the pHTPY6 vector via the EcoR I and Xho I cloning sites. Subsequently, the following primers, i.e., forward primers 5'-AATTCG-CAAGTATTCCTAGCAGTGCT-3' (SEQ ID NO: 28), 5'-CGCAAGT ATTCCTAGCAGTGCT-3' (SEQ ID NO: 29), and backward primers 5'-GTAC CTGTAGATACTT GGTAATTGGC-3' (SEQ ID NO: 30) and 5'-CTGTAG ATACTTGGTAATTGGC-3' (SEQ ID NO: 31) were used to generate a DNA fragment (containing the EcoR I and Kpn I cloning sites) that encodes the starch-binding domain (SBD) of glucomylase derived from fungi *Rhizopus* ssp, using the SBD-encoding gene as a template. See US Patent Publication 20060198792. The PCR product was then ligated into the pHTPY6 vector via the EcoR I and Kpn I cloning sites to form the pHTPY7 vector.

A DNA fragment encoding enhanced green fluorescent protein (EGFP), prepared by the sticky-end PCR method described in Zeng, Biotechniques 25:206-208 (1998) and Shih et al., Protein Sci. 11:1714-1719 (2002), was cloned into the pHTPY7 vector via cloning sites Pst I and Xho I to generate pHTPY7-EGFP expression plasmid.

An *E. coli* expression plasmid was constructed as follows. The following two primers were used to amplify a DNA fragment encoding the undecaprenyl diphosphate synthase (UPPs, see Pan et al., *Biochemistry* 39:10936-10942, 2000) and the cleavage site of SARS-CoV 3CL$^{pro}$ (Ala-Val-Leu-Gln (SEQ ID NO: 4), encoded by the underlined nucleotide sequence in the primers): 5'-GGTATT GAGGGTCGCGC GGTGCTGCAGATGTTGTCTGCTACTCAACC-3' (SEQ ID NO: 32) and reverse primer 5'-AGAGGAGAGTTA-GAGCCTCAGGCTGTTTC ATCACC-3' (SEQ ID NO: 33). The PCR product was cloned into the pET32Xa/Lic vector to produce the expression plasmid pET32Xa/Lic-UPPs.

Figure 2:
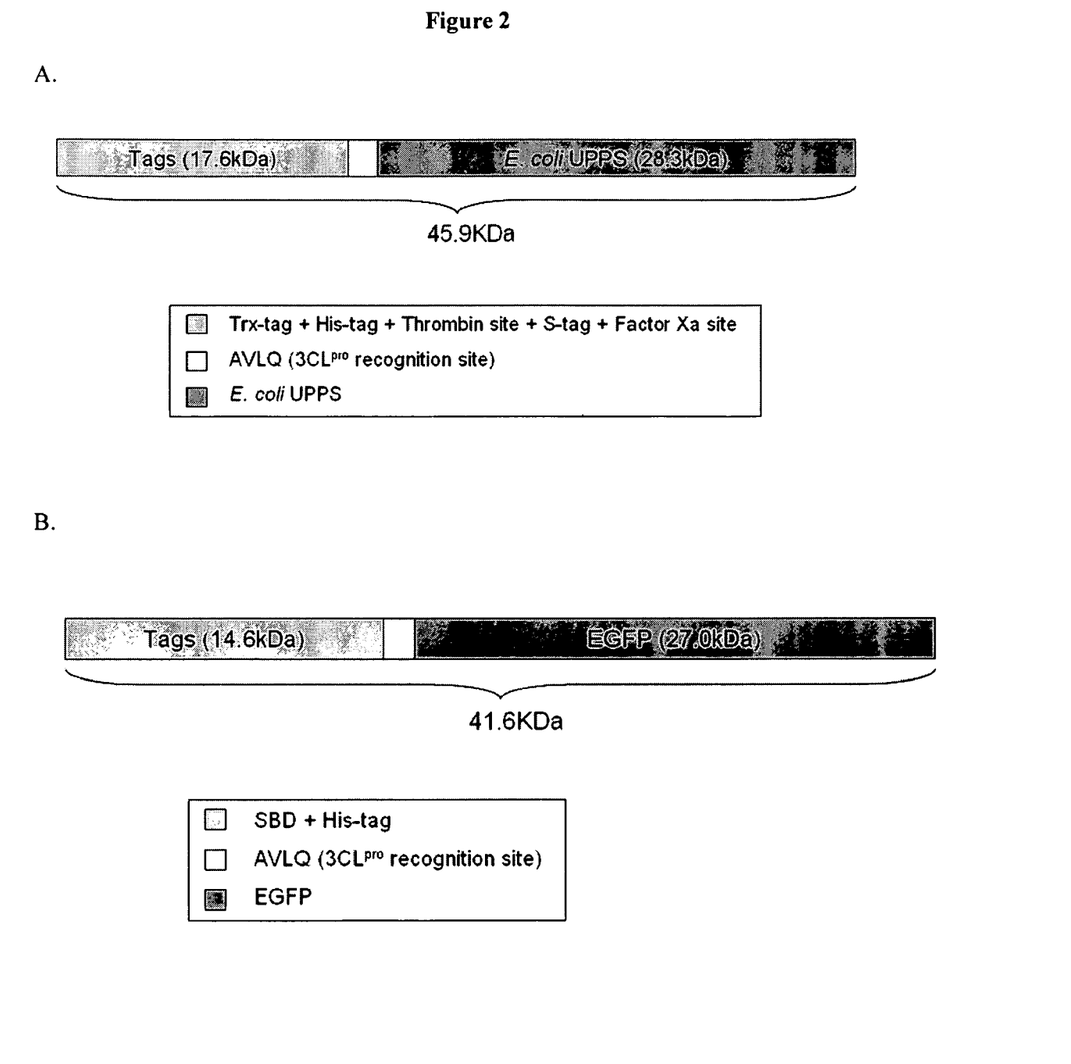
FIG. 2 is a schematic diagram showing the structures of fusion proteins produced in the protein expression system described herein. A: A fusion protein containing a number of protein tags, a cleavage site recognizable by the T25G mutant, and the E. coli undecaprenyl diphosphate synthase (UPPs). B: A fusion protein containing two protein tags, a cleavage site recognizable by the T25G mutant, and an enhanced green fluorescent protein (EGFP). 'AVLQ' is disclosed as SEQ ID NO: 4.

The expression plasmids pET32Xa/Lic-UPPs and pHTPY7-EGFP mentioned above were introduced into an *E. coli* host cell and a yeast *Pichia* host cell, respectively, for expression of fusion proteins His-Thioredoxin (Trx)-AV-LQM-UPPs ('AVLQM' disclosed as SEQ ID NO: 6) (see FIG. 2, Panel A) and His-SBD-AVLQM-EGFP ('AVLQM' disclosed as SEQ ID NO: 6) (see FIG. 2, Panel B), M being the N-terminal amino acid residue of both and UPPs and EGFP. The fusion proteins were purified using a NiNTA column. 5 μg of each purified fusion protein was treated by 0.1 μM the wild-type SARS-CoV 3CL$^{pro}$ or 0.1 μM the T25G mutant at 37° C. for 90 minutes to release free EGFP and UPPs. Only the T25G mutant cleaved both fusion proteins between the SBD tag and EGFP and between the His-Trx tag and UPPs. These results indicate that this protease mutant recognizes the cleavage site AVLQM (SEQ ID NO: 6) and cut precisely between Q and M in the cleavage site.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A recombinant protease comprising an amino acid sequence of a mutated severe acute respiratory syndrome-associated coronavirus 3C-like protease (SARS-CoV 3CL$^{pro}$), which comprises G at a position corresponding to $T_{25}$ in the wild type SARS-CoV 3CL$^{pro}$ (SEQ ID NO:1), wherein the recombinant protease recognizes the cleavage site $P_4P_3P_2QP_{1'}$ (SEQ ID NO:36) and cleaves between Q and $P_{1'}$, in which each of $P_4$ and $P_3$, independently, is A, V, G, L, or I; $P_2$ is L, V, or F; and $P_{1'}$ is G, A, V, L, I, S, T, M, C, D, E, Q, N, W, Y, or F, and wherein the amino acid sequence of the mutated SARS-CoV 3CL$^{pro}$ is at least 95% identical to SEQ ID NO:1.

2. The recombinant protease of claim 1, wherein the mutated SARS-CoV 3CL$^{pro}$ has the amino acid sequence of SEQ ID NO:2.

3. The recombinant protease of claim 1, wherein the recombinant protease recognizes the cleavage site AVLQM (SEQ ID NO:6) and cleaves between Q and M.

4. A method for preparing a target protein, comprising
providing a polypeptide, a portion of which is a target protein, the polypeptide including the amino acid sequence $P_4P_3P_2QP_{1'}$ (SEQ ID NO:36), wherein $P_{1'}$ is selected from the group consisting of G, A, V, L, I, S, T, M, C, D, E, Q, N, W, Y, and F and is the N-terminal residue of the target protein; $P_2$ is selected from the group consisting of L, V, and F; and each of $P_3$ and $P_4$, independently, is selected from the group consisting of A, V, G, L, and I, and
contacting the polypeptide with the recombinant protease of claim 1 to yield the target protein.

5. The method of claim 4, wherein $P_{1'}$ is V, L, I, M, C, D, E, Q, N, W, Y, or F.

6. The method of claim 5, wherein the amino acid sequence of $P_4P_3P_2QP_{1'}$ (SEQ ID NO:36) is AVLQM (SEQ ID NO:6).

7. The method of claim 4, wherein a fragment of the polypeptide is a protein tag, which is located at the N-terminus of the polypeptide.

8. The method of claim 5, wherein the recombinant protease has the amino acid sequence of SEQ ID NO:2.

9. A kit for producing a recombinant target protein, comprising an expression vector, containing a first nucleotide sequence encoding the amino acid sequence $P_4P_3P_2Q$ (SEQ ID NO:37), each of $P_4$ and $P_3$, independently, being A, V, G, L, or I, and $P_2$ being L, V, or F, wherein the 3' end of the first nucleotide sequence is a restriction site for cloning a gene encoding a target protein, and
a mutated severe acute respiratory syndrome-associated coronavirus 3C-like protease (SARS-CoV 3CL$^{pro}$), which comprises G at a position corresponding to $T_{25}$ in the wild type SARS-CoV 3CL$^{pro}$ (SEQ ID NO:1) being replaced by G in the mutated SARS-CoV 3CL$^{pro}$, or a nucleic acid encoding the mutated SARS-CoV 3CL$^{pro}$, wherein the mutated SARS-CoV 3CL$^{pro}$ recognizes the cleavage site of $P_4P_3P_2QP_{1'}$ (SEQ ID NO:36) and cleaves between Q and $P_{1'}$, in which $P_{1'}$ is G, A, V, L, I, S, T, M, C, D, E, Q, N, W, Y, or F, and wherein the amino acid sequence of the mutated SARS-CoV 3CL$^{pro}$ is at least 95% identical to SEQ ID NO:1.

10. The kit of claim 9, wherein the expression vector contains a nucleotide sequence encoding the amino acid sequence of AVLQ (SEQ ID NO:4) and the mutated SARS-CoV 3CL$^{pro}$ recognizes the cleavage site AVLQP$_{1'}$ (SEQ ID NO:34).

11. The kit of claim 9, wherein the expression vector further contains a second nucleotide sequence encoding a protein tag, the second nucleotide sequence being located upstream to the first nucleotide sequence.

12. The kit of claim 9, wherein the mutated SARS-CoV 3CL$^{pro}$ has the amino acid sequence of SEQ ID NO:2.

* * * * *

```
                       SEQUENCE LISTING

<160> NUMBER OF SEQ ID NOS: 37

<210> SEQ ID NO 1
<211> LENGTH: 306
<212> TYPE: PRT
<213> ORGANISM: SARS coronavirus

<400> SEQUENCE: 1

Ser Gly Phe Arg Lys Met Ala Phe Pro Ser Gly Lys Val Glu Gly Cys
1               5                   10                  15

Met Val Gln Val Thr Cys Gly Thr Thr Thr Leu Asn Gly Leu Trp Leu
            20                  25                  30

Asp Asp Thr Val Tyr Cys Pro Arg His Val Ile Cys Thr Ala Glu Asp
        35                  40                  45

Met Leu Asn Pro Asn Tyr Glu Asp Leu Leu Ile Arg Lys Ser Asn His
    50                  55                  60

Ser Phe Leu Val Gln Ala Gly Asn Val Gln Leu Arg Val Ile Gly His
65                  70                  75                  80

Ser Met Gln Asn Cys Leu Leu Arg Leu Lys Val Asp Thr Ser Asn Pro
                85                  90                  95

Lys Thr Pro Lys Tyr Lys Phe Val Arg Ile Gln Pro Gly Gln Thr Phe
            100                 105                 110
```

```
Ser Val Leu Ala Cys Tyr Asn Gly Ser Pro Ser Gly Val Tyr Gln Cys
        115                 120                 125

Ala Met Arg Pro Asn His Thr Ile Lys Gly Ser Phe Leu Asn Gly Ser
        130                 135                 140

Cys Gly Ser Val Gly Phe Asn Ile Asp Tyr Asp Cys Val Ser Phe Cys
145                 150                 155                 160

Tyr Met His His Met Glu Leu Pro Thr Gly Val His Ala Gly Thr Asp
                165                 170                 175

Leu Glu Gly Lys Phe Tyr Gly Pro Phe Val Asp Arg Gln Thr Ala Gln
                180                 185                 190

Ala Ala Gly Thr Asp Thr Thr Ile Thr Leu Asn Val Leu Ala Trp Leu
                195                 200                 205

Tyr Ala Ala Val Ile Asn Gly Asp Arg Trp Phe Leu Asn Arg Phe Thr
210                 215                 220

Thr Thr Leu Asn Asp Phe Asn Leu Val Ala Met Lys Tyr Asn Tyr Glu
225                 230                 235                 240

Pro Leu Thr Gln Asp His Val Asp Ile Leu Gly Pro Leu Ser Ala Gln
                245                 250                 255

Thr Gly Ile Ala Val Leu Asp Met Cys Ala Ala Leu Lys Glu Leu Leu
                260                 265                 270

Gln Asn Gly Met Asn Gly Arg Thr Ile Leu Gly Ser Thr Ile Leu Glu
                275                 280                 285

Asp Glu Phe Thr Pro Phe Asp Val Val Arg Gln Cys Ser Gly Val Thr
                290                 295                 300

Phe Gln
305

<210> SEQ ID NO 2
<211> LENGTH: 306
<212> TYPE: PRT
<213> ORGANISM: SARS coronavirus

<400> SEQUENCE: 2

Ser Gly Phe Arg Lys Met Ala Phe Pro Ser Gly Lys Val Glu Gly Cys
1               5                   10                  15

Met Val Gln Val Thr Cys Gly Thr Gly Thr Leu Asn Gly Leu Trp Leu
                20                  25                  30

Asp Asp Thr Val Tyr Cys Pro Arg His Val Ile Cys Thr Ala Glu Asp
                35                  40                  45

Met Leu Asn Pro Asn Tyr Glu Asp Leu Leu Ile Arg Lys Ser Asn His
        50                  55                  60

Ser Phe Leu Val Gln Ala Gly Asn Val Gln Leu Arg Val Ile Gly His
65                  70                  75                  80

Ser Met Gln Asn Cys Leu Leu Arg Leu Lys Val Asp Thr Ser Asn Pro
                85                  90                  95

Lys Thr Pro Lys Tyr Lys Phe Val Arg Ile Gln Pro Gly Gln Thr Phe
                100                 105                 110

Ser Val Leu Ala Cys Tyr Asn Gly Ser Pro Ser Gly Val Tyr Gln Cys
        115                 120                 125

Ala Met Arg Pro Asn His Thr Ile Lys Gly Ser Phe Leu Asn Gly Ser
        130                 135                 140

Cys Gly Ser Val Gly Phe Asn Ile Asp Tyr Asp Cys Val Ser Phe Cys
145                 150                 155                 160

Tyr Met His His Met Glu Leu Pro Thr Gly Val His Ala Gly Thr Asp
                165                 170                 175
```

```
Leu Glu Gly Lys Phe Tyr Gly Pro Phe Val Asp Arg Gln Thr Ala Gln
            180                 185                 190

Ala Ala Gly Thr Asp Thr Thr Ile Thr Leu Asn Val Leu Ala Trp Leu
            195                 200                 205

Tyr Ala Ala Val Ile Asn Gly Asp Arg Trp Phe Leu Asn Arg Phe Thr
            210                 215                 220

Thr Thr Leu Asn Asp Phe Asn Leu Val Ala Met Lys Tyr Asn Tyr Glu
225                 230                 235                 240

Pro Leu Thr Gln Asp His Val Asp Ile Leu Gly Pro Leu Ser Ala Gln
                    245                 250                 255

Thr Gly Ile Ala Val Leu Asp Met Cys Ala Ala Leu Lys Glu Leu Leu
            260                 265                 270

Gln Asn Gly Met Asn Gly Arg Thr Ile Leu Gly Ser Thr Ile Leu Glu
            275                 280                 285

Asp Glu Phe Thr Pro Phe Asp Val Val Arg Gln Cys Ser Gly Val Thr
            290                 295                 300

Phe Gln
305
```

```
<210> SEQ ID NO 3
<211> LENGTH: 5
<212> TYPE: PRT
<213> ORGANISM: Artificial sequence
<220> FEATURE:
<223> OTHER INFORMATION: Synthetic peptide

<400> SEQUENCE: 3

Ala Leu Val Gln Met
1               5

<210> SEQ ID NO 4
<211> LENGTH: 4
<212> TYPE: PRT
<213> ORGANISM: Artificial sequence
<220> FEATURE:
<223> OTHER INFORMATION: Synthetic peptide

<400> SEQUENCE: 4

Ala Val Leu Gln
1

<210> SEQ ID NO 5
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 5
gcggtgctgc ag                                                         12

<210> SEQ ID NO 6
<211> LENGTH: 5
<212> TYPE: PRT
<213> ORGANISM: Artificial sequence
<220> FEATURE:
<223> OTHER INFORMATION: Synthetic peptide

<400> SEQUENCE: 6

Ala Val Leu Gln Met
1               5

<210> SEQ ID NO 7
```

```
<211> LENGTH: 6
<212> TYPE: PRT
<213> ORGANISM: Artificial sequence
<220> FEATURE:
<223> OTHER INFORMATION: Synthetic 6xHis tag

<400> SEQUENCE: 7

His His His His His His
1               5

<210> SEQ ID NO 8
<211> LENGTH: 5
<212> TYPE: PRT
<213> ORGANISM: Artificial sequence
<220> FEATURE:
<223> OTHER INFORMATION: Synthetic peptide

<400> SEQUENCE: 8

Ala Val Leu Gln Ser
1               5

<210> SEQ ID NO 9
<211> LENGTH: 54
<212> TYPE: DNA
<213> ORGANISM: Artificial sequence
<220> FEATURE:
<223> OTHER INFORMATION: Synthetic primer

<400> SEQUENCE: 9
ggtgcatggt acaagtaacc tgtggaactg gaactcttaa tggattgtgg ttgg        54

<210> SEQ ID NO 10
<211> LENGTH: 54
<212> TYPE: DNA
<213> ORGANISM: Artificial sequence
<220> FEATURE:
<223> OTHER INFORMATION: Synthetic primer

<400> SEQUENCE: 10
ccaaccacaa tccattaaga gttccagttc cacaggttac ttgtaccatg cacc        54

<210> SEQ ID NO 11
<211> LENGTH: 39
<212> TYPE: DNA
<213> ORGANISM: Artificial sequence
<220> FEATURE:
<223> OTHER INFORMATION: Synthetic primer

<400> SEQUENCE: 11
catgccatgg ccagtggttt taggaaaatg gcattcccg                         39

<210> SEQ ID NO 12
<211> LENGTH: 54
<212> TYPE: DNA
<213> ORGANISM: Artificial sequence
<220> FEATURE:
<223> OTHER INFORMATION: Synthetic primer

<400> SEQUENCE: 12
ccgctcgagc ggtcaatgat gatgatgatg atgttggaag gtaacaccag agca        54

<210> SEQ ID NO 13
<211> LENGTH: 14
<212> TYPE: PRT
<213> ORGANISM: Artificial sequence
<220> FEATURE:
<223> OTHER INFORMATION: Synthetic peptide
```

```
<400> SEQUENCE: 13

Lys Thr Ser Ala Val Leu Gln Ser Gly Phe Arg Lys Met Glu
1               5                   10

<210> SEQ ID NO 14
<211> LENGTH: 10
<212> TYPE: PRT
<213> ORGANISM: Artificial sequence
<220> FEATURE:
<223> OTHER INFORMATION: Synthetic peptide

<400> SEQUENCE: 14

Ser Ala Val Leu Gln Glu Gly Phe Arg Lys
1               5                   10

<210> SEQ ID NO 15
<211> LENGTH: 10
<212> TYPE: PRT
<213> ORGANISM: Artificial sequence
<220> FEATURE:
<223> OTHER INFORMATION: Synthetic peptide

<400> SEQUENCE: 15

Ser Ala Val Leu Gln Phe Gly Phe Arg Lys
1               5                   10

<210> SEQ ID NO 16
<211> LENGTH: 10
<212> TYPE: PRT
<213> ORGANISM: Artificial sequence
<220> FEATURE:
<223> OTHER INFORMATION: Synthetic peptide

<400> SEQUENCE: 16

Ser Ala Val Leu Gln Gly Gly Phe Arg Lys
1               5                   10

<210> SEQ ID NO 17
<211> LENGTH: 10
<212> TYPE: PRT
<213> ORGANISM: Artificial sequence
<220> FEATURE:
<223> OTHER INFORMATION: Synthetic peptide

<400> SEQUENCE: 17

Ser Ala Val Leu Gln His Gly Phe Arg Lys
1               5                   10

<210> SEQ ID NO 18
<211> LENGTH: 10
<212> TYPE: PRT
<213> ORGANISM: Artificial sequence
<220> FEATURE:
<223> OTHER INFORMATION: Synthetic peptide

<400> SEQUENCE: 18

Ser Ala Val Leu Gln Lys Gly Phe Arg Lys
1               5                   10

<210> SEQ ID NO 19
<211> LENGTH: 10
<212> TYPE: PRT
<213> ORGANISM: Artificial sequence
<220> FEATURE:
<223> OTHER INFORMATION: Synthetic peptide

<400> SEQUENCE: 19
```

Ser Ala Val Leu Gln Leu Gly Phe Arg Lys
1               5                   10

<210> SEQ ID NO 20
<211> LENGTH: 10
<212> TYPE: PRT
<213> ORGANISM: Artificial sequence
<220> FEATURE:
<223> OTHER INFORMATION: Synthetic peptide

<400> SEQUENCE: 20

Ser Ala Val Leu Gln Met Gly Phe Arg Lys
1               5                   10

<210> SEQ ID NO 21
<211> LENGTH: 10
<212> TYPE: PRT
<213> ORGANISM: Artificial sequence
<220> FEATURE:
<223> OTHER INFORMATION: Synthetic peptide

<400> SEQUENCE: 21

Ser Ala Val Leu Gln Pro Gly Phe Arg Lys
1               5                   10

<210> SEQ ID NO 22
<211> LENGTH: 10
<212> TYPE: PRT
<213> ORGANISM: Artificial sequence
<220> FEATURE:
<223> OTHER INFORMATION: Synthetic peptide

<400> SEQUENCE: 22

Ser Ala Val Leu Gln Ser Gly Phe Arg Lys
1               5                   10

<210> SEQ ID NO 23
<211> LENGTH: 11
<212> TYPE: PRT
<213> ORGANISM: Artificial sequence
<220> FEATURE:
<223> OTHER INFORMATION: Synthetic peptide

<400> SEQUENCE: 23

Ser Ala Val Leu Gln Trp Glu Gly Phe Arg Lys
1               5                   10

<210> SEQ ID NO 24
<211> LENGTH: 72
<212> TYPE: DNA
<213> ORGANISM: Artificial sequence
<220> FEATURE:
<223> OTHER INFORMATION: Synthetic oligonucleotide

<400> SEQUENCE: 24
tcgaaaaaag agaggctgaa gctgaattct gcagctcgag cgtggcccag ccggccgtct      60
cggatcggta cg                                                          72

<210> SEQ ID NO 25
<211> LENGTH: 72
<212> TYPE: DNA
<213> ORGANISM: Artificial sequence
<220> FEATURE:
<223> OTHER INFORMATION: Synthetic oligonucleotide

<400> SEQUENCE: 25
tcgacgtacc gatccgagac ggccggctgg gccacgctcg agctgcagaa ttcagcttca      60

```
gcctctcttt tt                                                        72

<210> SEQ ID NO 26
<211> LENGTH: 72
<212> TYPE: DNA
<213> ORGANISM: Artificial sequence
<220> FEATURE:
<223> OTHER INFORMATION: Synthetic oligonucleotide

<400> SEQUENCE: 26
aattcacggg taccgcccag ccggcccacc accaccacca ccacggagga ggaactagtg    60
cggtgctgca gc                                                        72

<210> SEQ ID NO 27
<211> LENGTH: 72
<212> TYPE: DNA
<213> ORGANISM: Artificial sequence
<220> FEATURE:
<223> OTHER INFORMATION: Synthetic oligonucleotide

<400> SEQUENCE: 27
tcgagctgca gcaccgcact agttcctcct ccgtggtggt ggtggtggtg ggccggctgg    60
gcggtacccg tg                                                        72

<210> SEQ ID NO 28
<211> LENGTH: 26
<212> TYPE: DNA
<213> ORGANISM: Artificial sequence
<220> FEATURE:
<223> OTHER INFORMATION: Synthetic primer

<400> SEQUENCE: 28
aattcgcaag tattcctagc agtgct                                         26

<210> SEQ ID NO 29
<211> LENGTH: 22
<212> TYPE: DNA
<213> ORGANISM: Artificial sequence
<220> FEATURE:
<223> OTHER INFORMATION: Synthetic primer

<400> SEQUENCE: 29
cgcaagtatt cctagcagtg ct                                             22

<210> SEQ ID NO 30
<211> LENGTH: 26
<212> TYPE: DNA
<213> ORGANISM: Artificial sequence
<220> FEATURE:
<223> OTHER INFORMATION: Synthetic primer

<400> SEQUENCE: 30
gtacctgtag atacttggta attggc                                         26

<210> SEQ ID NO 31
<211> LENGTH: 22
<212> TYPE: DNA
<213> ORGANISM: Artificial sequence
<220> FEATURE:
<223> OTHER INFORMATION: Synthetic primer

<400> SEQUENCE: 31
ctgtagatac ttggtaattg gc                                             22
```

<210> SEQ ID NO 32
<211> LENGTH: 47
<212> TYPE: DNA
<213> ORGANISM: Artificial sequence
<220> FEATURE:
<223> OTHER INFORMATION: Synthetic primer

<400> SEQUENCE: 32
ggtattgagg gtcgcgcggt gctgcagatg ttgtctgcta ctcaacc      47

<210> SEQ ID NO 33
<211> LENGTH: 35
<212> TYPE: DNA
<213> ORGANISM: Artificial sequence
<220> FEATURE:
<223> OTHER INFORMATION: Synthetic primer

<400> SEQUENCE: 33
agaggagagt tagagcctca ggctgtttca tcacc      35

<210> SEQ ID NO 34
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: Gly, Ala, Val, Leu, Ile, Ser, Thr, Met, Cys,
      Asp, Glu, Gln, Asn, Trp, Tyr, or Phe

<400> SEQUENCE: 34

Ala Val Leu Gln Xaa
1               5

<210> SEQ ID NO 35
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 35
gcggtgctgc agatg      15

<210> SEQ ID NO 36
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: Ala, Val, Gly, Leu, or Ile
<220> FEATURE:
<221> NAME/KEY: MOD_RES
<222> LOCATION: (3)..(3)
<223> OTHER INFORMATION: Leu, Val, or Phe
<220> FEATURE:
<221> NAME/KEY: MOD_RES
<222> LOCATION: (5)..(5)
<223> OTHER INFORMATION: Gly, Ala, Val, Leu, Ile, Ser, Thr, Met, Cys,
      Asp, Glu, Gln, Asn, Trp, Tyr, or Phe

<400> SEQUENCE: 36

Xaa Xaa Xaa Gln Xaa
1               5

```
<210> SEQ ID NO 37
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: Ala, Val, Gly, Leu, or Ile
<220> FEATURE:
<221> NAME/KEY: MOD_RES
<222> LOCATION: (3)..(3)
<223> OTHER INFORMATION: Leu, Val, or Phe

<400> SEQUENCE: 37

Xaa Xaa Xaa Gln
1
```